(12) United States Patent
Hosel et al.

(10) Patent No.: US 6,635,420 B1
(45) Date of Patent: Oct. 21, 2003

(54) PURIFICATION OF SUBSTANCES FROM A BIOLOGICAL SAMPLE

(75) Inventors: Wolfgang Hosel, Tutzing (DE); Helmut Lenz, Tutzing (DE); Jochen Peter, Waiblingen (DE)

(73) Assignee: Roche Diagnostics GmbH (DE)

( * ) Notice: Subject to any disclaimer, the term of this patent is extended or adjusted under 35 U.S.C. 154(b) by 0 days.

(21) Appl. No.: 09/508,138

(22) PCT Filed: Aug. 31, 1998

(86) PCT No.: PCT/EP98/05521

§ 371 (c)(1),
(2), (4) Date: Oct. 13, 2000

(87) PCT Pub. No.: WO99/13330

PCT Pub. Date: Mar. 18, 1999

(30) Foreign Application Priority Data

Sep. 8, 1997 (DE) .......................................... 197 39 218

(51) Int. Cl.⁷ ........................ G01N 33/53; G01N 33/543
(52) U.S. Cl. ................ 435/6; 435/4; 435/7.1; 435/7.9; 435/7.92; 435/7.94; 435/174; 435/176; 435/177; 435/803; 435/810; 435/814; 435/815; 435/971; 435/975; 436/63; 436/501; 436/518; 436/513; 436/523; 436/524; 436/527; 436/528; 436/532; 436/534; 436/536; 436/823; 436/824
(58) Field of Search .................... 435/7.1, 7.9, 7.92, 435/6, 7.94, 174, 4, 176, 177, 803, 810, 814, 815, 971, 975; 436/501, 523, 527, 536, 513, 518, 532, 63, 524, 528, 534, 823, 824

(56) References Cited

U.S. PATENT DOCUMENTS

| 4,624,930 | A | * | 11/1986 | Tanswell et al. | ............ 435/7.94 |
| 4,732,848 | A | * | 3/1988 | Lenz et al. | .................... 435/25 |
| 5,614,367 | A | * | 3/1997 | Kaluza et al. | ............. 435/69.6 |
| 5,614,394 | A | * | 3/1997 | Hoyle et al. | ............. 424/152.1 |

FOREIGN PATENT DOCUMENTS

| EP | 0 378 197 A3 | 7/1990 | .......... G01N/33/82 |
| EP | EP 0 440 044 A1 | * 8/1991 | |
| EP | 0 506 032 A1 | 9/1992 | ............ C07K/3/18 |
| WO | WO 92/02818 | 2/1992 | ......... G01N/33/543 |
| WO | WO 99/13330 | 3/1999 | .......... G01N/33/53 |

OTHER PUBLICATIONS

"Guide to Protein Purification," Methods in Enzymology 182:366–375 (1990).

* cited by examiner

*Primary Examiner*—Long V. Le
*Assistant Examiner*—Kartic Padmanabhan
(74) *Attorney, Agent, or Firm*—Marilyn L. Amick; Roche Diagnostics Corporation

(57) ABSTRACT

The invention concerns a method for the purification of a target substance from a biological sample by immobilizing the target substance on a solid phase by means of a high affinity binding pair and subsequently eluting it by adding a partner of the binding pair in a free form. In addition reagent kits for carrying out the method are disclosed.

20 Claims, 3 Drawing Sheets

SEQUENCE LISTING

```
<160> NUMBER OF SEQ ID NOS: 2

<210> SEQ ID NO 1
<211> LENGTH: 25
<212> TYPE: DNA
<213> ORGANISM: Artificial Sequence
<220> FEATURE:
```

-continued

```
<223> OTHER INFORMATION: Description of Artificial Sequence: Primer

<400> SEQUENCE: 1
tatccggcct ttattcacat tcttg                                             25

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 2
ccagcggcat cagcacctt                                                    19
```

PURIFICATION OF SUBSTANCES FROM A BIOLOGICAL SAMPLE

Figure 1:
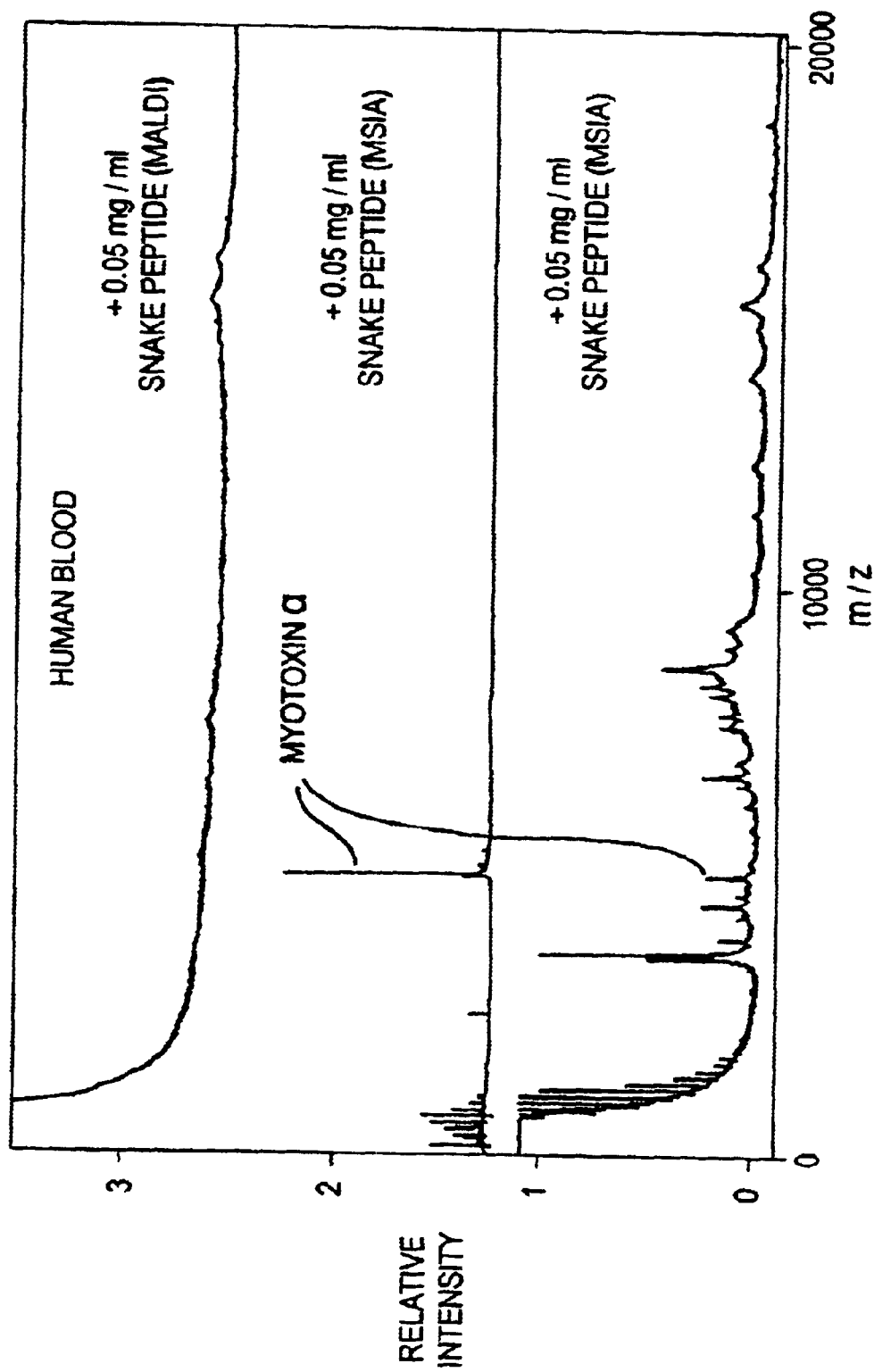

This application claims priority to parent application DE 1039218 filed Sep. 8, 1997, now German patent no. 19739218, granted Mar. 11, 1999, and to PCT application no. PCT/EP98/05521 filed Aug. 31, 1998 and published as WO 9913330 on Mar. 18, 1999.

BACKGROUND

The invention concerns a method for the preparative purification of a target substance from a biological sample by immobilizing the target substance on a solid phase by means of a high affinity binding pair and subsequently eluting it by adding a partner of the binding pair in a free form. In addition reagent kits for carrying out the method are disclosed.

The immunosorptive purification of biological substances, e.g. macromolecules such as proteins, is a method that has been known for a long time which allows the efficient isolation of such substances from complex biological materials like serum, urine or cell lysates (Eveleigh and Levy, J. Solid-phase Biochem. 2 (1977), 45–78; Cooper, "Biochemische Arbeitsmethoden", pp. 222–241 (1981), Walter de Gruyter, Berlin; Pharmacia Fine Chemicals, Affinity Chromatography: Principles and Methods (1983), pp 92–95; Wawrazynczak and Cumber, in: Immunochemical Protocols, M. M. Manson ed. Methods in Molecular Biology 10, chapter 32 (1992), Humana Press, Totowa, N.J. USA). The desorption of the substances bound to the immobilized antibodies is usually achieved with unspecific methods e.g. by adding buffers with a low (<2.5) or high (>10) pH value, chaotropic reagents such as urea or guanidine hydrochloride, organic solvents or detergents to the elution buffer.

In some cases specific desorption methods have also been described e.g. to isolate haptens by displacement with a hapten analogue or to isolate proteins by displacement with a low molecular peptide. However, such specific desorption processes are an exception in immunosorptive processes since they can only be carried out at all with a very limited number of substances. Hence the unspecific desorption methods described above are mainly used and especially elution at a low pH such as e.g. with 1 M propionic acid.

However, in immunosorptive purification methods from biological materials it has been shown that the biomolecules that are present e.g. proteins in some cases also bind unspecifically to the immunoadsorber to a considerable extent i.e. not via an antibody-antigen interaction. If the desorption is unspecific, e.g. using an acidic buffer, these substances are then also eluted from the immunoadsorber and are present in addition to the desired substance as an impurity. This is a particular disadvantage especially when the substance to be purified is only present at a very low concentration since it then only represents a small proportion of the overall material that is eluted from the immunoadsorber so that additional laborious purification steps are necessary before the desired substance is available in sufficient purity, if this is possible with the very small amounts of substance that may be present.

Thus for example the prostate-specific antigen (PSA) is present in human serum at a concentration of ca. 1 to 1500 ng/ml, whereas other proteins such as human serum albumin (HSA) are present at a $10^5$ to $10^7$-fold higher concentration of ca. 70 mg/ml. Since these proteins bind unspecifically to the immunoadsorber, when a substance such as PSA that is present at very low concentration is purified by immunosorption, the desired substance may only represent a very small proportion of the eluted total protein as a result of unspecific desorption and for example may not be identifiable at all in a gel electrophoretic separation of the eluate (cf. e.g. FIG. 2). In this case it may not be possible to characterize the protein or only with great difficulty e.g. after a protease digestion due to the presence of the contaminating proteins. Similar problems also occur with other analytical methods such as e.g. mass spectrometry since also in this case the analysis is very difficult or impossible due to the many contaminating proteins especially when the exact mass of the protein to be examined is unknown. Thus although a combination of MALDI-TOF mass spectroscopy and immunosorption has been described in which the immunosorptively-bound material is eluted through the acidic MALDI matrix (cinnamic acid derivatives dissolved in trifluoroacetic acid/acetonitrile) and is measured directly (Nelson et al., Anal. Chem. 67 (1995), 1153–1158). However, it is clear that when the substance to be purified is only present at very low concentrations, numerous other proteins occur some of which result in considerably higher signals than the desired target substance (cf. FIG. 1 taken from Krone et al., Mass Spectrometric Immunoassay, Poster Session ABRF'96: Biomolecular Techniques (1996), San Francisco, USA).

DESCRIPTION

Hence the object of the present invention was to find a generally applicable method for purifying substances from biological samples in which the disadvantages of the prior art are at least partially eliminated. In particular the method should utilize the advantages of specific immunosorption while avoiding the disadvantages of unspecific desorption. In particular the method according to the invention should enable an elution in an essentially neutral pH range to avoid damage to the target substance associated with a loss of immune reactivity or/and biological activity by extreme pH values.

This object is achieved by a method for purifying a target substance from a sample comprising the steps:
   a) adsorbing the target substance onto a solid phase in which the binding of the target substance to the solid phase comprises the interaction between a first and a second partner of a high affinity binding pair, and the first partner of the binding pair is bound directly or indirectly to the target substance and the second partner of the binding pair is bound to the solid phase,
   b) separating non-adsorbed sample components from the solid phase,
   c) contacting the solid phase with the first partner of the binding pair or with an analogue thereof in a free form resulting in a desorption of the target substance from the solid phase and
   d) separating the target substance from the solid phase.

A first preferred embodiment of the invention is a method for purifying a target substance from a sample comprising the steps:
   a) Providing a solid phase with an immobilized reactant $R_1$ where $R_1$ contains at least one group that can bind specifically to the target substance and at least one group comprising a first partner of a high affinity binding pair, and the binding of $R_1$ to the solid phase occurs by means of an immobilized reactant $R_2$ which contains a group comprising the second partner of the high affinity binding pair, b) contacting the sample with the solid phase resulting in an adsorption of the target substance onto the solid phase via a binding to $R_1$, c) separating non-adsorbed sample components from the solid phase d) contacting the solid phase with the first partner of the binding pair or with an analogue thereof in a free form resulting in a desorption of the target substance as a complex with $R_1$ from the solid phase and e) separating the complex from the solid phase.

Figure 2:
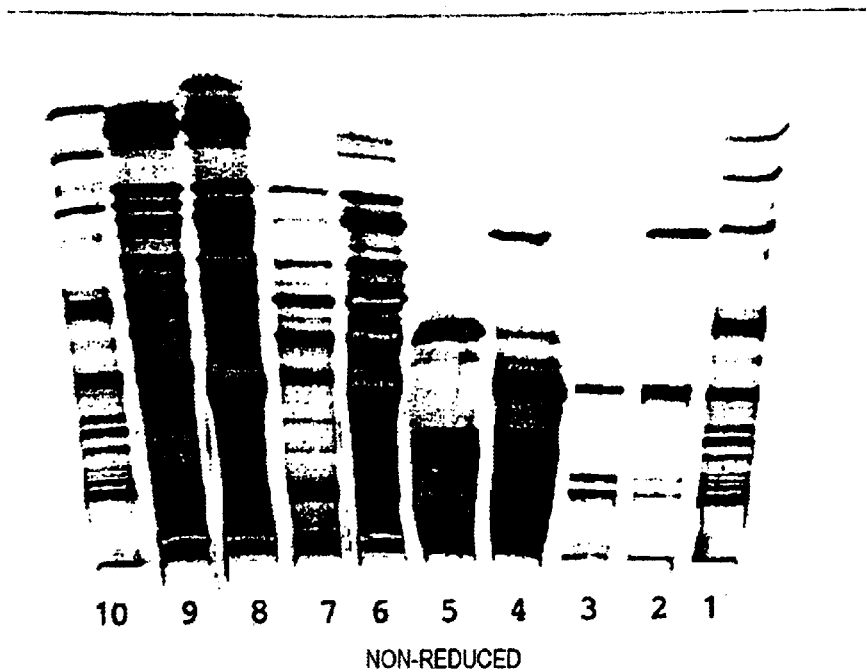

In this embodiment of the method according to the invention a reactant $R_1$ is used that can bind specifically to the target substance to be purified and which is coupled to a first partner of a high affinity binding pair e.g. a hapten. In addition a second reactant $R_2$ is used which can bind specifically to the first binding partner and contains the second partner of the binding pair e.g. an anti-hapten antibody and has such an affinity for the first binding partner that the reactant $R_1$ can be efficiently displaced by the first binding partner in a free form or by a derivative thereof. Elution with the free first binding partner enables the complex composed of the reactant $R_1$ and the substance to be detected to be very specifically eluted from the solid phase and free from unspecifically adsorbed impurities. The principle and result of this purification method and a comparison with an unspecific acidic elution is shown in FIG. 2 using the isolation of PSA and a PSA/ACT complex from human serum as an example.

The purification principle according to the invention can also be used to directly isolate a substance if this can be provided with a first binding partner whose presence does not interfere with the further analysis or use of this substance. Examples of this are shown for the isolation of double-labelled DNA and of fusion proteins.

Hence a second preferred embodiment of the invention concerns a method for purifying a target substance to which a first partner of a high affinity binding pair is bound, from a sample comprising the steps:

a) providing a solid phase which contains an immobilized second partner of a high affinity binding pair, b) contacting the sample with the solid phase resulting in an adsorption of the target substance onto the solid phase by means of a binding between the first and the second partner of the binding pair, c) separating non-adsorbed sample components from the solid phase, d) contacting the solid phase with the first partner of the binding pair or with an analogue thereof in a free form resulting in a desorption of the target substance from the solid phase and e) separating the target substance from the solid phase.

The principle of specifically detaching a hapten/anti-hapten immune complex from a solid phase to purify substances from biological samples was previously unknown. Although Ishikawa (European Patent Application No. 88 112 927.4) indeed describes a quantitative immunoassay in which a complex of anti-dinitrophenyl (DNP)-antibody/DNP-labelled-anti-analyte antibody/analyte/anti-analyte-antibody-enzyme conjugate immobilized on a polystyrene particle is released by adding dinitrophenyl. The released immune complex is bound to a second polystyrene particle which contains a receptor directed against the haptenized antibody and is determined quantitatively by means of the enzymatic activity. In contrast to the method described by Ishikawa, the present invention is not directed towards the removal of a labelled reagent present in the measuring medium but rather it targets the accompanying substances that are present in a very high excess in a biological sample in addition to a substance to be purified. It was therefore previously not foreseeable whether the desorption step described by Ishikawa could be used at all for the selective removal of these accompanying substances. This is particularly true because in the method according to the invention there is preferably a direct analysis of the substance detached from the immunoadsorber and not a further purification step comprising a specific binding to an additional solid phase as described by Ishikawa. It was surprisingly found that such an additional binding is not necessary for an efficient purification but rather that an excellent separation of accompanying substances is already observed in the solution eluted specifically from the first solid phase.

The method according to the invention can be used for all purification problems in which substances, in particular biological molecules, which are mainly present at a very low concentration have to be purified from complex biological samples such as body fluids e.g. whole blood, plasma, serum, urine, sputum etc. from animal or plant tissues, soil samples or cell extracts or from molecular biological reaction mixtures. The substance to be purified is a biomolecule in the widest sense i.e. a component occurring in a biological sample. Examples of such substances are cells, cell fractions, cell organelles, viral particles, polypeptides, peptides, glycoproteins, lipoproteins, polysaccharides, nucleic acids, hormones, metabolites, neurotransmitters and mediators. Preferred examples of substances to be purified are polypeptides and nucleic acids such as DNA or RNA molecules.

According to a first preferred embodiment of the invention a target substance is purified which does not have to be coupled to a first partner of a high affinity binding pair. This embodiment of the method according to the invention is especially suitable for the purification of non-modified, target substances which occur naturally in biological samples. According to a second preferred embodiment of the method according to the invention a target substance which is already coupled to a first partner of a high affinity binding pair is purified. This embodiment of the method is especially suitable for the purification of target substances from molecular biological reaction mixtures that are modified with corresponding groups e.g. hapten-modified nucleic acids from amplification mixtures, or for the purification of recombinant polypeptides.

The solid phase used in the method according to the invention can contain any support materials known from the prior art. Particulate solid phases such as magnetic microparticles are preferred.

The reactant $R_1$ used in the first embodiment is preferably a conjugate comprising at least one group that can bind specifically to the substance to be purified 8 and at least one group comprising the first partner of a high affinity binding pair. $R_1$ preferably contains only one group of the first binding pair. The group that can specifically bind can, depending on the type of substance to be detected, be an antibody directly against the substance, a nucleic acid that is complementary with the substance to be detected, a lectin or biological receptor which binds specifically to the substance to be detected. The group that can bind specifically is preferably an antibody (and this term also includes antibody fragments or antibody derivatives) or a nucleic acid (in which case this term also includes nucleic acid analogues such as peptidic nucleic acids).

An essential feature of the method according to the invention is that the target substance bound to the solid phase can be eluted by contacting the solid phase with the first partner of the binding pair or with an analogue thereof in a free or soluble form. The partners of the binding pair are preferably selected such that this elution can be achieved under physiological pH conditions e.g. in a pH range of 5 to 8. In addition it is preferred that the partners of the binding pair are selected such that the affinity constant between the first and the second partner of the binding pair is in the range of $10^6$ l/mol to $10^{10}$ l/mol so that a high affinity binding is achieved. In order to enable a good displacement by the first binding partner in a free form, the binding between the first and second binding partner should have an adequate reversibility.

A low molecular substance with a maximum molecular weight of up to preferably 4 kD and particularly preferably up to 2 kD is preferably used as the first partner of the binding pair. An example of this is a hapten group in which case an antibody directed against the hapten group is used as the second partner of the binding pair. Examples of suitable haptens are molecules which are able to produce an immune response in an organism which leads to the production of specific anti-hapten antibodies. Specific examples of haptens are steroids such as progesterone or synthetic derivatives thereof, cardenolides such as digoxin or digoxigenin, fluorescent dyes such as fluorescein or derivatives thereof, hormones such as thyroid hormones e.g. T3 or T4, drugs such as barbiturates or theophyllin, metal complexes in particular electrochemiluminescent metal complexes such as ruthenium or rhodium-(bispyridyl)$_3$ complexes or other compounds such as dinitrophenol or diphenylhydantoin. Substances against which highly specific antibodies already exist such as digoxigenin, fluorescein, dinitrophenol, thyroid hormones, ruthenium or rhodium complexes, theophyllin, barbiturates or diphenylhydantoin are particularly preferred.

Furthermore a sugar, in particular a monosaccharide or oligosaccharide, can be used as the first reactant of the binding pair and a lectin can be used as the second partner of the binding pair. Thus for example a sugar containing a mannose group can be used as the first binding partner and concanavalin A as the second binding partner.

In addition a low molecular receptor ligand can also be used as the first partner of the binding pair and a biological receptor can be used as the second partner of the binding pair. Examples of such binding pairs are acetycholine/acetylcholine receptor or histamine/histamine receptor.

In yet a further preferred embodiment a peptide epitope is used as the first partner of the binding pair and an antibody directed against the peptide epitope is used as the second partner of the binding pair.

A peptide epitope which forms the first partner of the binding pair can on the one hand, like a hapten, sugar or receptor ligand be bound to the reactant $R_1$ or to the target sequence by coupling in the form of an activated derivative e.g. of an active ester. If the reactant $R_1$ or the target substance is a nucleic acid, the first binding partner can also be introduced by an enzymatic reaction e.g. by using labelled primers, labelled oligonucleotide building blocks or/and attaching labelled nucleic acid fragments. If the reactant $R_1$ or the target substance is a peptide or polypeptide, a peptide epitope can also be introduced into $R_1$ or into the target substance as a first partner of the binding pair by genetic engineering.

The target substance or the complex composed of $R_1$ and the target substance is eluted from the solid phase by contacting the solid phase with the first partner of the binding pair or with an analogue thereof in a free or soluble form. An elution that is as quantitative as possible can be achieved if the free first partner of the binding pair is used in a molar excess relative to the first partner of the binding pair bound to $R_1$. This molar excess is preferably in the range of at least 50-fold, particularly preferably 100–500-fold.

In addition the elution from the solid phase can be improved by using the free first partner of the binding pair in the form of a conjugate comprising a carrier molecule and several molecules of the first partner of the binding pair that are coupled to it. Examples of suitable carrier molecules are polypeptides such as polylysine, albumin, unspecific antibodies etc. or polysaccharides such as dextrins. Several molecules of the first partner of the binding pair can be coupled to this carrier molecule using known methods e.g. using activated derivatives of the first partner. Examples of such conjugates are polyhaptenylated carrier molecules such as polylysine-digoxigenin, bovine serum albumin-digoxigenin etc.

Another method of improving elution from the solid phase is to use an analogue of the first partner of the binding pair bound to $R_1$ as the free first partner of the binding pair in which this free analogue has a higher binding affinity for the second partner of the binding pair than that of the first partner of the binding pair bound to $R_1$ or the target substance. Hence, if the first partner of the binding pair is a hapten, a modified hapten can be used as the analogue for which the second partner of the binding pair has a higher affinity than for the bound hapten. Thus digoxigenin can be used as the bound hapten group and an anti-digoxin antibody as the binding partner and digoxin as the free binding partner. Analogous examples are the use of nitrophenol as the bound hapten, an anti-dinitrophenol antibody and dinitrophenol as free hapten, the use of T3 as the bound hapten, anti-T4 antibody and free T4 or the use of a rhodium-bispyridyl$_3$ complex as the bound hapten, an anti-rhodium-(bispyridyl)$_3$ complex antibody and rhodium-(bispyridyl)$_3$ complex as the free hapten.

The elution can also be improved when the same group is used as the free and bound binding partner but each has a different linker. Thus a group hapten-linker 1 can be used as the bound partner together with an antibody directed against hapten-linker 2 and the group hapten-linker 2 can be used as the free binding partner. In the case of peptide epitopes a first peptide sequence can be used as the bound partner, an antibody directed against a second peptide sequence which differs from the first sequence by an amino acid and the second peptide sequence can be used as the free binding partner.

After elution from the solid phase the target substance can be analysed e.g. by HPLC, gel electrophoresis or mass spectroscopy. Further purification steps can be optionally carried out e.g. release of the substance to be purified from the complex with the reactant $R_1$. In addition undesired parts of the substance to be purified can be removed by cleavage. Thus for example in the case of fusion proteins, undesired parts can be separated by proteolytic cleavage for example with enterokinase, factor Xa or IgA protease.

A specific application of the method according to the invention is the purification of recombinant peptides or polypeptides e.g. eukaryotic peptides or polypeptides which are produced in bacterial cells e.g. in *E. coli* cells. Here one can produce fusion polypeptides which contain a first domain which can bind specifically to the reactant $R_1$ and a second desired target domain. A protease cleavage site can be introduced between the first and second domain such that the fusion polypeptide can be cleaved proteolytically e.g. with an immobilized protease after desorption. The reactant $R_1$ remaining in the reaction mixture containing the bound first domain of the fusion polypeptide can be separated in a subsequent step by binding to an immobilized reactant such that the desired target domain is obtained in a pure form.

In the case that the target substance e.g. a peptide or polypeptide target domain should be examined without cleavage of the complex $R_1$ which was used for the isolation and the first domain, an additional detection group can be introduced on $R_1$ which is structurally different from the first partner of the binding pair. Binding to a solid phase can be achieved with the aid of this additional group e.g. via the system biotin/streptavidin or hapten/anti-hapten antibody, or a conjugate can be attached for the detection e.g. biotin/streptavidin enzyme (for example peroxidase or alkaline phosphatase), hapten/anti-hapten-antibody enzyme. Alternatively a directly detectable marker group can also be used as the detection group e.g. a luminescent metal complex or a fluorescent dye.

Yet a further subject matter of the invention is a reagent kit for the purification of a target substance from a sample comprising:

a) a solid phase,
b) a reactant $R_1$ which contains at least one group that can specifically bind to the substance to be purified and at least one group comprising a first partner of a high affinity binding pair,
c) a reactant $R_2$ which contains a group comprising the second partner of the high affinity binding pair, and $R_2$ is bound to the solid phase or contains a group which can bind to the solid phase,
d) the first partner of the binding pair or an analogue thereof in a free form.

An additional reagent kit is provided to introduce the first binding partner into a target substance and to subsequently purify the target substance comprising:

a) a solid phase,
$b_i$) a first partner of a high affinity binding pair in a form which is suitable for introduction into a target substance
$b_{ii}$) means for introducing the first partner of the binding pair into the target substance,
c) the second partner of the binding pair bound to the solid phase and
d) the first partner of the binding pair or an analogue thereof in a free form.

Preferred embodiments with respect to the components of the reagent kit are elucidated above. The components (a), (b) and (c) can be present as a single reagent or as several separate reagents. Component (d) is present separated from the other components. The components of the reagent kit can be present in any desired form e.g. as packaged units, lyophilisates, solutions, suspensions etc. The reagent kit is preferably used in a method as described above.

The invention is further elucidated by the following examples and figures.

DRAWINGS

FIG. 1: (Upper trace) Normal MALDI mass spectrum of human blood to which 0.05 mg/ml of a snake peptide (Myotoxin a) was added. (Middle and lower traces) MALDI spectra after binding the snake peptide to an anti-Myotoxin a-antibody and elution with the acidic MALDI matrix. The numerous unspecifically bound peptides and proteins from the blood which were eluted with the acidic matrix and which in some cases have considerably higher signals than Myotoxin a can be clearly seen in the lower trace where only 0.00002 mg/ml Myotoxin a had been added.

FIG. 2: Comparison of the gel electrophoretic separations of PSA immunoadsorbed from prostate carcinoma plasma and a PSA/ACT complex after detachment with various elution agents. In each case a plasma sample without PSA and PSA/ACT was run as a control.

Figure 3:
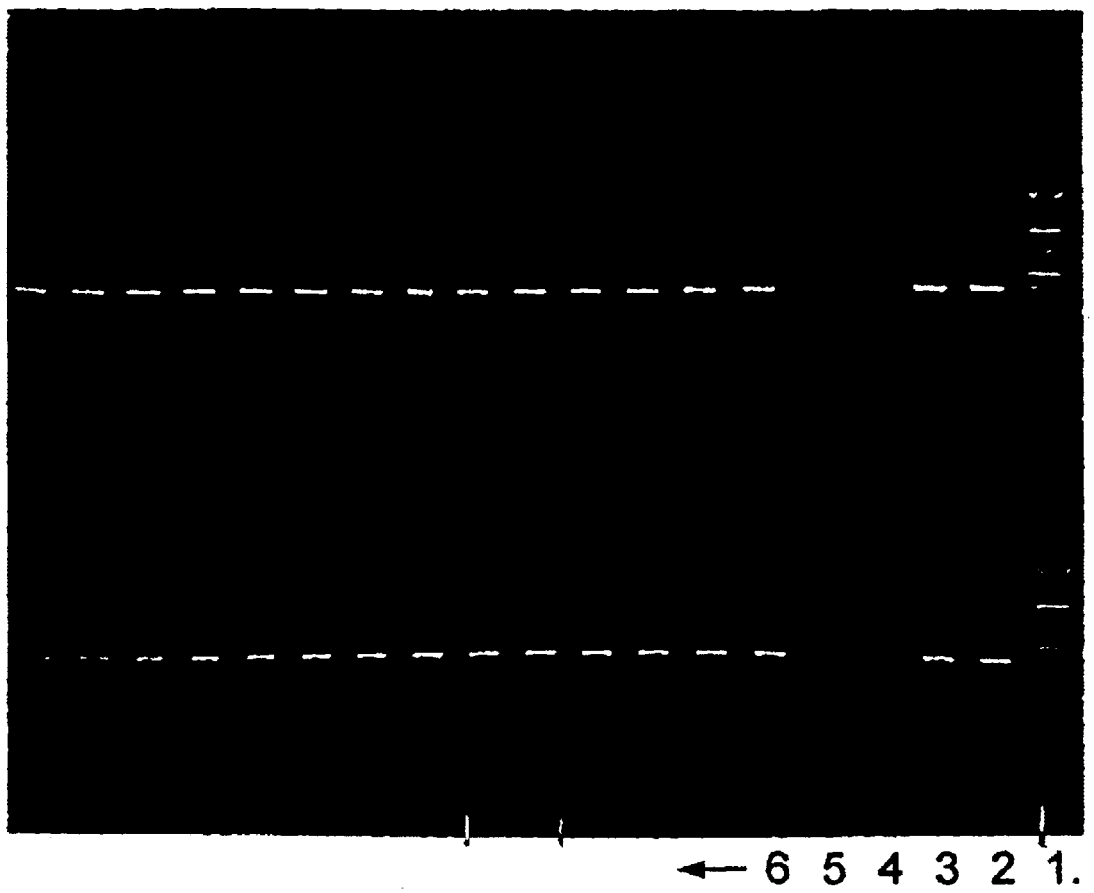

FIG. 3: Result of an agarose gel electrophoresis of DIG-labelled PCR products after detachment with digoxigenin-lysine.

EXPERIMENTAL EXAMPLES

Example 1

Immunosorptive Isolation of PSA From Human Serum: Comparison of the Elution with a Hapten and with Acids The immunosorptions are each carried out on streptavidin-coated magnetic beads. 1 ml of a bead suspension (0.72 mg/ml) is used for each sample. The beads are washed three times with 1 ml wash solution each time (phosphate buffered saline solution PBS, pH 7.2) before adding the samples, and the supernatant was removed after separating the beads with a magnet. Six mixtures with the following composition are each added to one aliquot of beads:

Mixtures 1 and 2: (1) 500 µl monoclonal antibody (MAB) anti-digoxigenin-IgG, biotinylated (50 µg/ml) and (2) 500 µMAB anti-PSA-IgG, digoxigenylated (50 µg/ml)

Mixtures 3 to 6: 500 µl MAB anti-PSA-Fab', biotinylated (16.6 µg/ml)

After adding each solution they are incubated for 60 min at room temperature while shaking. Solutions (1) and (2) are each added sequentially to the mixtures 1 and 2. Subsequently the beads are separated from the supernatant, washed four times with wash solutions and the supernatant is removed.

Then 0.5 ml sample (plasma) is added to the individual mixtures. Plasma without PSA is used as a control. After incubating for 60 min and subsequently washing four times as described above, the supernatants are removed and the following elution solutions are added:

Mixtures 1 and 2: 200 µl saturated digoxigenin-lysine HCl solution pH=7.2

Mixtures 3 and 4: 200 µl propionic acid 1 M

Mixtures 5 and 6: 200 µl fonnic acid/water/acetonitrile in a ratio of 1:3:2

The mixtures are shaken for 60 min at room temperature and the supernatants are lyophilized in a Speed Vac after separating the beads. The lyophilisates are then taken up in 10 µl water and used for an SDS polyacrylamide gel electrophoresis under non-reducing conditions and the result is shown in FIG. 3.

Result of the gel electrophoresis:

In mixtures 3 to 6 in which an acid elution was carried out in each case, very many protein bands from the human serum can be seen which are due to unspecific binding to the magnetic beads and have been detached by the acidic elution agent. It can also be seen that the elution agent containing acetonitrile which is favourable for the subsequent MALDI-TOF-MS unspecifically detaches considerably more proteins than 1 M propionic acid. In contrast in the detachment with digoxigenin-lysine HCl only the IgG bands of the digoxigenylated anti-PSA MABs can be seen in addition to the desired bands for PSA and PSA/ACT as well as a small amount of serum albumin which is also detached to a slight extent in this specific elution of the beads due to its high concentration in the serum. Due to the large number of protein bands obtained in the acidic elution, it is very difficult to identify the specific target proteins in these gels. This also subsequently considerably impairs further analysis of such bands e.g. by MALDI-TOF-MS after a protease digestion.

Example 2

Use of Luminescent Metal Complexes as Haptens

An immunosorptive isolation of PSA from human serum was carried out analogously to the procedure described in example 1. Instead of digoxigenin, a ruthenium(bispyridyl)$_3$-complex and a rhodium(bispyridyl)$_3$ complex were used as haptens and corresponding anti-hapten antibodies. Elution was carried out by adding the free metal complexes.

A specific elution was found as in example 1.

Example 3

Isolation of a Fusion Protein

A fusion protein was constructed which was composed of a protein 1 or peptide 1 against which a digoxigenylated antibody is available as well as the desired target protein 2. After recombinant expression of this fusion protein e.g. in E. coli, a cell lysis is carried out. The homogenate is shaken for one hour while stirring at room temperature with the magnetic streptavidin beads described above which are loaded with an anti-digoxigenin MAB. After magnetic separation the pure complex composed of the digoxigenylated antibody and the fusion protein are located in the supernatant. If there is a protease cleavage site between part 1 and 2 of the fusion protein e.g. for enterokinase it is possible to use this enzyme to cleave the fusion protein. After separation of the digoxigenylated antibody with protein 1 bound to it e.g. with protein A-Sepharose, the pure target protein 2 is present in the solution.

The digoxigenylated antibody can carry an additional detection group e.g. a hapten that is different from digoxigenin. This additional detection group can be used for immobilization or detection by binding to an anti-hapten antibody.

Example 4

Specific Desorption of Digoxigenylated DNA

The immunosorptions were carried out on microtitre plates coated with polyclonal anti-Dig-antibody (AD-MATP, Boehringer Mannheim product, cat. Mo. 1 754 289). A 397 bp long PCR fragment (0.1 pmol/μl) of the chloramphenicol gene (CAT) is used as the DNA; primer 1 (TAT CCG GCC TTT ATT CAC ATT CTT G) is labelled with 5' digoxigenin and primer 2 (CCA GCG GCA TCA GCA CCT T) is labelled with 5' biotin.

A) Desorption Detection with PCR

50 μl aliquots of CAT fragment diluted 1:10000 in buffer (100 mmol/l sodium phosphate pH 7.5, 50 mmol/l NaCl, 0.5 mmol/l EDTA, 1% casein, 0.1% Tween 20 and 0.02% MIT) containing 0.1 mg/ml herring DNA are bound to AD-MTP in 8 duplicate mixtures for 30 min at room temperature while shaking. They are washed 10 times with 250 μl wash buffer (PBS containing 0.1% Tween).

The elution is carried out by adding 50 μl ready-to-use PCR mixture (PCR mastermix containing 0.4 pmol/μl primers 1 and 2) which contains 50% to 0.78% Dig-lysine saturated redistilled water (1:2 dilution series) at 37° C. for 1 h while shaking. Buffer without Dig-lysine is used as a negative control and a solution containing 50% Dig-lysine and 1 μl 1:200 diluted CAT fragment is used as the positive control.

Subsequently the following PCR program was run with the mixtures:

denature: 94° C., 2 min

20× or 25×: 94° C., 10 sec, 68° C., 30 sec final extension: 72° C., 7 min

10 μl aliquots of each PCR mixture are analysed by a 1.5% agarose gel electrophoresis. As shown in FIG. 3 the generated CAT fragment is found in all Dig-lysine containing PCR mixtures after 20 (upper row) or 25 (lower row) cycles analogous to the positive control (lanes 2 and 3 from the right). The negative control (lanes 4 and 5 from the right) remains empty as expected.

B) Desorption Detection with ELISA

100 μl aliquots of CAT fragment (gene bank ACC.NO.X65321) diluted 1:1000 in DNA conjugate dilution buffer (100 mmol/l sodium phosphate pH 7.5, 50 mmol/l NaCl, 0.5 mmol/l EDTA, 1% casein, 0.1% Tween 20 and 0.02% MIT (methylisothiazolone) and one sample without CAT are bound for 30 min at room temperature while shaking to AD microtitre plates in seven duplicate mixtures. They are washed five times with 250 μl wash buffer.

The elution is carried out by adding 100 μl PBS containing 10% to 0.001% Dig-lysine saturated redistilled water (1:10 dilution series) as well as a 100% control without Dig-lysine at 37° C. for 1 h while shaking.

Subsequently it is washed as described above and detected for 30 min with 100 μl streptavidin-peroxidase conjugate (200 mU/ml) in dilution buffer. Then it is washed again as described above and developed with 100 μl TMB substrate (tetramethylbenzidine). The reaction is stopped with 50 μl 1 M H$_2$SO$_4$ and measured in an ELISA reader at 450 nm.

Evaluation of the ELISA data show a specific desorption of the Dig-labelled DNA.

What is claimed is:

1. A method for purifying a target substance from a sample comprising the steps of:
   (a) providing a solid phase with an immobilized reactant $R_1$ wherein $R_1$ comprises at least one group that binds specifically to said target and at least one group comprising a first partner of a binding pair, wherein the binding pair is characterized by having an affinity constant from about $10^6$ l/mol to $10^{10}$ l/mol, and wherein binding of $R_1$ to said solid phase occurs by means of an immobilized reactant $R_2$ which comprises a group comprising a second partner of said binding pair,
   (b) contacting said sample with said solid phase resulting in adsorption of said target onto said solid phase via binding to $R_1$,
   (c) separating non-adsorbed sample components from said solid phase,
   (d) contacting said solid phase with a first partner of said binding pair or analog thereof in free form resulting in desorption of said target as a complex with $R_1$ from said solid phase, and
   (e) separating said complex from said solid phase.

2. The method of claim 1, wherein said target is selected from the group consisting of cells, cell fractions, cell organelles, viral particles, polypeptides, peptides, glycoproteins, lipoproteins, polysaccharides, nucleic acids, hormones, metabolites, neurotransmitters and mediators.

3. The method of claim 1, wherein said target is selected from the group consisting of polypeptides and nucleic acids.

4. The method of claim 1, wherein said solid phase is a particulate solid phase.

5. The method of claim 1, wherein said group $R_1$ is selected from the group consisting of antibodies and nucleic acids.

6. The method of claim 1, wherein said first partner is a hapten group and said second partner is an antibody directed against said hapten group.

7. The method of claim 6, wherein said first partner is selected from the group consisting of digoxigenin, fluorescein, dinitrophenol, thyroid hormones, ruthenium and rhodium-(bispyridyl)$_3$ complexes, theophylline, barbiturates and diphenylhydantoin.

8. The method of claim 1, wherein said first partner is a sugar and said second partner is a lectin.

9. The method of claim 6, wherein said first partner is a sugar containing a mannose group and said second partner is concanavalin A.

10. The method of claim 1, wherein said first partner is a receptor ligand having a maximum molecular weight of 4 kD and said second partner is a biological receptor.

11. The method of claim 1, wherein said first partner is a peptide epitope and said second partner is an antibody directed against said epitope.

12. The method of claim 1, wherein said desorption is carried out at a pH of 5 to 8.

13. The method of claim 1, wherein said first partner in free form is in molar excess relative to said bound first partner.

14. The method of claim 1, wherein said first partner in free form is a conjugate comprising a carrier molecule coupled to multiple molecules of said first partner.

15. The method of claim 1, wherein said first partner in free form is an analog of said bound first partner and said analog has a higher binding affinity for said second partner than said bound first partner.

16. The method of claim 1, additionally comprising the step of releasing said substance from said complex with $R_1$.

17. The method of claim 1, wherein said reactant $R_1$ carries a detection group that is different from said first partner.

18. The method of claim 1, wherein said target substance is a recombinantly produced polypeptide.

19. The method of claim 18, wherein said recombinantly produced polypeptide is a fusion polypeptide comprising a first domain which binds specifically to said first partner and a second domain which binds specifically to said target.

20. The method of claim 9, wherein said polypeptide further comprises a protease cleavage site between said first and second domains.

* * * * *